United States Patent
Galvez et al.

(10) Patent No.: US 6,342,582 B1
(45) Date of Patent: Jan. 29, 2002

(54) REACTION AND DISSOLVING MEDIUM FOR PEPTIDES AND SYNTHESIS METHOD USING THIS MEDIUM

(75) Inventors: Marie Galvez, Toussieu; Marie-France Maurice, Caluire, both of (FR)

(73) Assignee: Rhodia Chimie, Courbevoie (FR)

( * ) Notice: Subject to any disclaimer, the term of this patent is extended or adjusted under 35 U.S.C. 154(b) by 0 days.

(21) Appl. No.: 09/096,510

(22) Filed: Jun. 12, 1998

Related U.S. Application Data

(62) Division of application No. 08/208,190, filed on Mar. 10, 1994, now Pat. No. 5,798,443, which is a continuation of application No. 07/998,758, filed on Dec. 30, 1992, now abandoned, which is a continuation of application No. 07/621,468, filed on Dec. 4, 1990, now abandoned.

(30) Foreign Application Priority Data

Jul. 6, 1990 (FR) .............................. 90 08593
Dec. 4, 1990 (FR) .............................. 89 15957

(51) Int. Cl.$^7$ ................................................ C07K 1/00
(52) U.S. Cl. ........................................ 530/333; 530/338
(58) Field of Search ................................ 530/333, 338, 530/344

(56) References Cited

U.S. PATENT DOCUMENTS

| | | | |
|---|---|---|---|
| 3,700,609 A | 10/1972 | Tregear et al. ................ | 260/2.5 |
| 3,860,631 A | 1/1975 | Gleason et al. .............. | 260/471 |
| 3,875,136 A * | 4/1975 | Kamber ..................... | 260/112.5 |
| 3,888,930 A | 6/1975 | Kleiner et al. ........... | 260/606.5 |
| 4,638,000 A | 1/1987 | Sugihara et al. ............ | 514/211 |
| 4,755,591 A | 7/1988 | Konig et al. ................ | 530/309 |
| 4,871,842 A | 10/1989 | Sugihara et al. ............ | 540/523 |
| 4,922,015 A | 5/1990 | Breipohl et al. ............ | 562/451 |

FOREIGN PATENT DOCUMENTS

GB  1182450  2/1970

OTHER PUBLICATIONS

Narita et al., Prediction and Improvement of Protected Peptide Solubility In Organic Solvents, Int. J. Peptide Protein Res. 24, 580–587 (1984).
Gross et al., The Peptides; Analysis, Synthesis, Biology 1, 45–64 (Academic Press 1979).
Mutter et al., The Peptides; Analysis, Synthesis, Biology, 2, 288–332 (Academic Press 1980).
Fuhrhop et al., Organic Synthesis, 4.1.2 peptides, 207–220 (Verlag Chemie, 1983).
Merrified, Solid Phase Peptide Synthesis. I. The Synthesis Of A Tetrapeptide, J.A.C.S., 85, 2149–2154 (1963).
Ueki et al., "Peptide Synthesis by Oxidation–Reduction Condensation. I. Use of NPS–Peptides as Amino Component". Bulletin Of The Chemical Society Of Japan, vol. 44, pp. 1108–1111 (1971).
Johnson et al., "The 4–(Methylthio)phenyl and 4–(Methylsulfonyl)phenyl Esters in the Preparation of Peptides and Polypeptides. Synthesis of the Protected Heptapeptide ($A_{82}$–$A_{88}$) of Bovine Chymotrypsinogen A", J. Org. Chem. 33, 4521–4524, (1968).
Dutta et al. "Polypeptides. Part XII. The Preparation of 2–Pyridyl Esters and Their Use in Peptide Synthesis", J. Chem. Soc. C 2896–2902, (1971).
Jakubke, "Darstellung N–geschützter Aminosaüreester des 8–Hydroxychinolins und deren Verwendung als reaktive Zwischenprodukts für die Peptidsynthese", Z. Natruforsch 20b 273–274 (1965).
Bodansky, "Principles of Peptide Synthesis", p. 30, (Springer–Verlag 1984).
Photaki et al., "On Cysteine and Cystine Peptides. Part V S–Trityl–and S–Diphenyl–methyl–cysteine and –cysteine Peptides", J. Chem. Soc. C, 2683–2687, (1970).
Fujii et al., "Studies on Peptides. LXXII. Examination of the $N^g$–Alkylation of Lysine in the Methanesullphonic Acid Procedure for Peptide Synthesis", Chem. Pharm. Bull. 25, 3096–3098, (1977).
Yajima et al., "LXXXI. Application of a New Arginine Derivative, $N^G$–Mesitylene–2–Sulfonylarginine, to the Synthesis of Substance P and Neurotensin", Int. J. Pept. Protein Res. 14, 169–176, (1979).
Bodansky, *"Principles of Peptide Synthesis"* pp. 28–34, (Springer–Verlag 1984).
Bodansky et al., "Coupling in the Absence of Tertiary Amines", Int. J. Pept. Prot. Res. 20, 387–395 (1982).
Bodanszky et al., "Coupling in the Absence of Tertiary Amines", CA 98 (13): 107742u (1982).

* cited by examiner

Primary Examiner—Christopher S. F. Low
Assistant Examiner—David Lukton
(74) Attorney, Agent, or Firm—Finnegan, Henderson, Farabow, Garrett & Dunner, L.L.P.

(57) ABSTRACT

The present invention relates to a reaction and dissolving medium for the synthesis of peptides. This reaction and dissolving medium for peptide synthesis and/or purification comprises a diluent A chosen from a group of water-immiscible solvents and a phenol B. By employing this reaction and dissolving medium, peptides can be synthesized which are useful as medicaments, vaccines, agrofoodstuff products or plant protection products.

14 Claims, No Drawings

REACTION AND DISSOLVING MEDIUM FOR PEPTIDES AND SYNTHESIS METHOD USING THIS MEDIUM

This a division of application Ser. No. 08/208,190, filed Mar. 10, 1994, now U.S. Pat. No. 5,798,443 which is a continuation of Ser. No. 07/998,758, filed Dec. 30, 1992 abandoned, which is a continuation of Ser. No. 07/621,468, filed on Dec. 4, 1990 abandoned, all of which are incorporated herein by reference.

BACKGROUND OF THE INVENTION

The present invention relates to a reaction and dissolving medium for the synthesis of peptides. It also relates to a method for the synthesis of peptides in said medium.

A large number of methods exist for the synthesis of peptides in liquid phase. They all have fundamental common features such as:

if necessary, protecting the function of the side chain of a peptide by a protective group cleavable at the end of the peptide synthesis;

protecting the amine function ($\alpha N$) of a peptide by a protective group cleavable after the condensation reaction;

activating the carboxylic acid function of a protected peptide; and then subjecting the peptide to a condensation reaction with a peptide in which the C-terminal function is protected and in which the amine function is free.

The peptide is obtained by total deprotection from protective groups after the condensation reaction of all of the amino acids.

The condensation reaction can be carried out either in homogeneous liquid phase or in heterogeneous phase (for example, the Merrifield synthesis).

In general, the synthesis of peptides requires the protection of the carboxylic function of the C-terminal amino acid in the form of esters.

In the case of peptide synthesis in homogeneous phase, the ester will be chosen from:

the methyl, -benzyl and tert-butyl esters;

the ester of polymers soluble in organic solvents,
for example the ester of polyethers described by M. Mutter et al., Justus Liebigs Annalen der Chemie 1975 pp. 901–915, hereby incorporated by reference;

or preferably from the esters disclosed in the French Patent Application No. FR 89 06700, which corresponds to U.S. Ser. No. 592,028, filed on Oct. 2, 1990, which discloses GPC esters and is hereby incorporated by reference.

In the case of peptide syntheses in the heterogeneous phase, the ester will be, in particular, an ester of polymers insoluble in organic solvents. The following polymers may be mentioned, without this list being limiting:

the styrene-divinylbenzene copolymer introduced by R. B. Merrifield (J.A.C.S. 1963, 85 p. 2149, 2154) hereby incorporated by reference;

co-Boc-$\beta$-Ala-N'-acroylyl-hexamethylenediamine polydimethylacrylamide described by E. Atherton and R. C. Sheppard (J.A.C.S. 97 1975 p. 6584, 6585), hereby incorporated by reference;

polystyrene grafted on Kel-F (Tregear et al. 1966, U.S. Pat. No. 3,700,609 and Chem. Abot. 71 p. 508241 (1969)), both of which are hereby incorporated by reference; and cellulose.

Peptide syntheses in heterogeneous phase may be carried out in a stirred reactor, in a column reactor or by any other technique (for example use of a membrane).

The yield and the purity of the final product to a large extent depend on the yield from each step, on the one hand because of the geometric growth in the losses and on the other hand because of the problems in separating the desired product from the by-products. This problem is amplified as the synthesis progresses when the number of amino acids increases.

Moreover, in the specific case where the condensation reaction is carried out in a homogeneous liquid medium, all of these methods have a common disadvantage: their productivity per unit volume is low because of the poor solubility of the amino acids or of the intermediate protected peptides.

This disadvantage is indicated by numerous authors, such as:

M. Narita, K. Ishikawa, J. Y. Chen and Y. Kin, Int. J. Peptide Protein Res., 24, 580 (1984).

E. Gross and J. Meienhofer, The Peptides; Analysis, Synthesis, Biology, Academic Press, 1, 45, (1979).

M. Mutter and E. Bayer, The Peptides; Analysis, Synthesis, Biology, Academic Press, 2, 288 (1980).

Fuhrhop and Penzcin, Organic Synthesis, Verlag Chemie, 4.1.2. Peptides, 219 (1984).

The productivity-per unit volume is in particular very low when water-immiscible solvents such as chloroform or ethyl acetate are used. By way of example, the 4-nitrobenzyl ester of $\alpha$-N-(2-nitrophenylsulfenyl)-$\omega$-N-benzylphenylalanyl-nitro-L-arginine is synthesized in an amount of 0.016 mol per liter in chloroform: E. Wünsch, Methoden der Organischem Chemie {Methods in Organic Chemistry}, XV-2, Synthese von Peptiden {Peptide Synthesis}, Georg Thieme Verlag, 108 (1974).

For its part, the methyl ester of benzyoxycarbonyl-L-prolyl-L-tyrosine has been prepared in a concentration of 0.050 mol per liter in ethyl acetate: M. Bodansky and A. Bodansky, The Practice of Peptide Synthesis, Springer-Verlag, 140, 1984.

The water-miscible solvents have specific disadvantages and are hardly more advantageous. In fact, although they sometimes allow the synthesis of peptides to be carried out in a more concentrated medium, they prohibit their direct purification by washing with water, which is necessary to remove the reagents introduced in excess and the products of the coupling reaction.

Consequently, the water-miscible solvents are usually distilled and then replaced by water-immiscible solvents in order to proceed with washing. This therefore comes back to the previous problem because the purification step requires very large volumes of solvent, while the treatment of the reaction mass has been made more complex by the introduction of supplementary distillation and redissolving operations.

Thus, the dipeptide Z-Cys(S-BZl)-Tyr OEt prepared in THF (2 mole/liter) has been transferred to ethyl acetate (0.1 mol/liter) before being washed with water. M. Bodansky, The Practice of Peptide Synthesis, Springer Verlag, 129, 1984.

The protected dipeptide Z-Lys(Z)-Gly-OEt synthesized in acetonitrile (0.13 mol/liter) has been purified after replacing the initial solvent by ethyl acetate (0.05 mol/liter) (Ibid. 150, 1984), while Z-Ala-Tyr-OCH$_3$ has been prepared in dimethylformamide (0.3 mol/liter) before being purified by washing with water, in a solution of ethyl acetate (0.1 mol/liter) (Ibid. 148, 1984).

The use of these water-miscible solvents, which generally are polar, can lead to additional disadvantages with respect to industrial hygiene (DMSO, HMPT), and with respect to the chemical selectivity. In general, the polar solvents in fact promote the racemization of the N-protected activated amino acid, according to the implementation by D. S. Kemp, Peptides, Analysis, Synthesis, Biology; 1, 354–355, 1979.

Thus, the production of concentrated solutions of peptide intermediates in organic solvents which are immiscible with water and compatible with current production standards (Good Manufacturing practice) remains an unresolved problem.

It is for this reason that one of the aims of the present invention is to provide a reaction medium which increases the yield from peptide condensation reactions. Another aim of the present invention is to provide a reaction medium which makes it possible to facilitate the syntheses and the purifications of peptides, in particular the peptides having 2 to 50 amino acids in general, and in particular 3 to 20 amino acids.

Finally, another aim is to provide a reaction medium allowing a peptide synthesis in homogeneous medium at high concentrations (for example at least about 0.1 and in general about 0.2 M, depending upon the number of amino acids in the peptide—shorter chain length peptides can of course be synthesized at higher molar concentrations than can longer chain length peptides).

These aims and others, which will become apparent from the text which follows, are achieved by means of a reaction and dissolving medium for peptide synthesis and/or purification which comprises a diluent A chosen from at least one of a group of water-immiscible diluents A and at least one phenol B.

In the present application, the term "phenol B" is defined to mean any hydroxyaromatic compound, including mixtures of hydroxyaromatic compounds. The term "water-immiscible diluent A" is defined to mean a diluent that is immiscible in water in some proportion. In other words, when the diluent is added to water, two phases should be formed.

The amount of phenol B is preferably at least 1/200 of the diluent A. There is no strict upper limit to the amount of phenol B to diluent A, however. Thus, the use of phenol B (pure product or mixture) without diluent A also forms part of the invention. However, it is preferred that if phenol B alone is used, that the following conditions are met:

the melting point of the phenol B is at most about 50° C. (in the present description the zeros are not significant numbers unless otherwise specified);

the phenol B can be separated from the reaction product by distillation, including, if necessary, distillation under reduced pressure;

the phenol B is not miscible with water in at least some proportion so that, among other things, two phases will exist in order that subsequent washing with aqueous compounds can be effected;

the phenol B does not form a stable emulsion capable of hindering the removal by washing with water of co-products formed from reactions between peptides.

The halogenophenols, advantageously dichlorophenols, and preferably monochlorophenols, and the lower alkyl phenols, for example, satisfy these criteria.

Although they may be used on their own, phenol B satisfying the criteria above also comprise one of the particularly valuable subclasses of phenol B which can be used in a mixture with the diluent A.

It is, however, preferable that there is at least one diluent A and at least one phenol B (which is different from diluent A). Advantageously, the ratio by mass of phenol B to said diluent A is between 1/200 and 1/1, preferably between 1/20 and 1/2.

The above values expressed as a mass ratio are suitable for phenol proper and for phenol B which have a molecular mass which is about that of phenol proper (i.e., not of an order of magnitude different from that of phenol proper ($C_6H_5OH$)).

For phenol B of high molecular weight, the concentration in mols per liter of diluent B is preferably $5 \times 10^{-2}$, more preferably between 0.1 and 2 M and most preferably between 0.5 and 1.5 M.

When the diluent A and phenol B are not miscible in each other in some proportion, the upper limit for the content of phenol B is the lower of the following two limits: that mentioned above (i.e., the upper limit for phenol B, either based on mass or by mole) and the solubility limit of the phenol B in the diluent A.

The diluent A is at least on(e organic solvent which is preferably sufficiently polar to dissolve at least about 1% and preferably at least about 2%, by mass, of phenol proper ($C_6H_5OH$) and is preferably sufficiently hydrophobic to be immiscible with water in some proportion.

It is preferable that water is able to dissolve only at most 10% of the diluent A, advantageously at most 1% by mass, this being the case even in the presence of phenol B.

The diluent A can be mixtures of diluents A and can include petroleum fractions. Of course, under the operating conditions, the diluent A should be substantially inert towards the phenol B and the peptide synthesis reagents used.

The preferred families of diluents A are chosen from the group comprising aromatic derivatives, ethers, esters and halogenated solvents, wherein the aromatic derivatives, ethers, esters and halogenated solvents ace defined so as not to overlap one another.

The following may be mentioned as paradigms of members of these families:

as halogenated aliphatic derivatives: dichloromethane, 1,2-dichloroethane and 1,1,1-trichloromethane;

as aromatic derivatives: toluene;

as halogenated aromatic derivatives: chlorobenzene;

as esters: ethyl acetate and isopropyl acetate; and as ethers: tert-butyl methyl ether, and anisole.

For reasons of industrial economy, it is preferable that the diluent A can be distilled under atmospheric pressure or under primary or secondary vacuum.

In general, the phenol B is chosen from at least one of the group of compounds corresponding to the following formula (I)

(I)

in which

Ar represents a monocyclic or polycyclic aromatic radical which may or may not be heterocyclic, the polycyclic ring system being either fused or not fused;

the substituent $R_1$, which can be the same or different, represents:

a halogen unit, preferably fluorine, chlorine or bromine, or a group —Z—$R_2$, where Z can be a single bond; or an oxygen atom;

where $R_2$ represents a hydrogen atom or an alkyl or aryl radical which may be hydroxylated or mono- or poly-halogenated and has at most 8 carbon atoms, where n represents the number of substituents and is 0 or an integer at most equal to the number of positions available for substitution on the aromatic nuclei;

and their mixtures.

The alkyl groups (as defined in the Duval Dictionary of Chemistry, Presses Scientifiques Internationale Paris VI 1959, hereby incorporated by reference) may preferably be straight-chain or branched aliphatic radicals having at most 6 carbon atoms or arylaliphatic radicals.

The number of positions available for substitution can easily be determined using simple rules known to those skilled in the art.

Thus, for example:

when Ar=phenyl$\leq 5$

Ar=pyridyl$\leq 4$

Ar=naphthyl$\leq 7$

Ar=quinolyl$\leq 6$

Advantageously, the phenol B has at most 30 carbon atoms, and preferably at most 20 carbon atoms.

It is desirable that the vicinal positions of the phenol B function are unsubstituted or occupied by non-obstructing groups.

The tertiary or secondary carbon radicals linked to said vicinal positions can be regarded as obstructing groups.

The monocyclic compounds are those which give the best effectiveness/cost compromise; those having 6 members (pyridinyl or phenyl ring) are preferred.

It is also desirable that Z—$R_2$ is a hydroxyl group no more than three times, and preferably no more than twice.

Advantageously, in the formula I, the radicals $R_1$ are chosen from the group comprising:

the methyl, ethyl, propyl and butyl radicals, the trifluoromethyl and pentafluoroethyl radicals, the methoxy, ethoxy, propoxy and butoxy radicals, phenyl, hydroxyphenyl and Ar—OH, where Ar is as defined above, the phenoxy and hydroxyphenoxy radicals, and fluorine, chlorine and bromine atoms In order not to make the phenol B molecule too heavy, it is desirable that n in the formula I is at most 5, preferably at most 3.

Amongst the phenol B giving the best results, it is expedient to mention:

hydroxypyridines, which may be monosubstituted, hydroxyquinolines, which may be monosubstituted, monohalogenophenols (preferably monochlorophenols), polyhalogenophenols (preferably polyfluorophenols), phenols monosubstituted or disubstituted by $C_1$ to $C_4$ alkyl radicals, $C_1$ to $C_4$ alkoxy radicals, $C_2$ to $C_2$ perfluoroalkyl radicals and 2,2,2-trifluoroethyl, diphenols, phenol proper, and naphthols, which may be monosubstituted or disubstituted.

It is preferred that the hydroxyaromatic compound not be nitrophenols, such as p-nitrophenol, 2,4-dinitrophenol or picric acid.

The media according to the present invention can enable an amino acid, which may be protected, to be dissolved to give a solution having a concentration of at least 0.05 M.

The amino acid may be C- or N-protected; in the latter case, the acid group may be activated on the acid function and can even be activated on the lateral acid function(s) (e.g. in the aspartic acid case). It is preferred that o-nitrophenylsulfenyl (NPS) protective groups not be used with the amino acids of the present invention.

The amino acids may be naturally occurring or synthetic.

The medium according to the present invention also enables a protected peptide to be dissolved. The medium according to the present invention also enables unprotected peptides (Pro-Gly-$NH_2$.HCl; His-Trp.HCl; Arg-Pro.2HCl) to be dissolved and the synthesis to be carried out.

Any peptides can-be made using the present invention. However, the peptide formed from the reaction of Copper (II) Bz-L-leucinate and and NPS-Gly-OEt is not preferred.

Because the medium according to the present invention can simultaneously dissolve amino acids, peptides and blocking or activating reagents, it allows blocking or activation of amino acids to be carried out "in situ". Thus, the medium according to the present invention can act as reagent when it comprises, in view to a successive or simultaneous introduction, in addition to the phenol B and the diluent A, peptides (including elementary amino acid) and possibly blocking and/or activating reagents.

For purposes of the present specification, the term peptide, includes an elementary amino acid.

The peptide (including an elementary amino acid) may be C- or N-protected; in the latter case, the acid group may be activated on the acid function.

Of course, the functions of the amino acids, other than the acid or amine functions addressed by the synthesis, may also be protected if necessary, in accordance with techniques customary in the art.

The medium of the present invention can enable the solubility of peptides in organic phase to be considerably increased. It is preferred, for instance, that the peptides are present in an amount such that there is at least one mole of total amino acid unit for every three moles of phenol B. For instance, a reaction between one mole of a dipeptide and one mole of a-tripeptide (i.e., a reaction which contains five total amino acid units) should contain at most 15 moles of phenol B. More preferably there should be at least one mole of total amino acid unit for every 2 moles of phenol 3, and even more preferably, at least one mole of total amino acid unit for every mole of phenol B. Most preferably, there should be at least 0.75 moles of total amino acid unit for every mole of phenol B.

In general, the present invention allows the order of magnitude of the solubility to be changed in a favorable sense, taking as the basis the solubility of the peptide in the diluent A in the absence of phenolic B.

The medium can enable the various steps of the peptide synthesis to be carried out under conditions allowing a good yield per unit volume. It can increase the productivity of the condensation steps in particular.

Amongst the numerous advantages of the medium according to the present invention, it is appropriate to emphasize that the condensation reactions of a N-protected and C-activated amino acid or peptide with an amino acid or a peptide which is not C-protected can be very greatly facilitated and accelerated when the reaction takes place in said medium. This can offer a very appreciable advantage for the synthesis of oligopeptides (up to about 20 members or even 50). This is one of the reasons why it is appropriate to make particular mention of the media according to the invention which can act as reagent and which can contain, as compounds with a view to a successive or simultaneous introduction:

a) a diluent A chosen from the group of water-immiscible solvents;

b) a phenol B; and c) a peptide of 1 to 50, or 3 to 50, or 5 to 50, advantageously 1 to 20, more preferably 3 to 20 and most preferably 5 to 20 amino acids, in which neither the terminal N nor the C terminal is protected.

The amount of phenol B is preferably at least 1/200 of the diluent A. There is no strict upper limit. Advantageously, the ratio by mass of the phenol B to the diluent A is between 1/200 and 1/1, preferably between 1/20 and 1/2.

The above values expressed as mass ratio are suitable for phenol proper and for phenol 3 which have a molecular mass which is about that of phenol proper (i.e., not of an order of magnitude different from that of phenol proper ($C_6H_5OH$)).

For the phenol B of high molecular weight, the concentration in mole per liter of diluent A is preferably $5 \times 10^{-2}$, more preferably between 0.1 and 2 and most preferably between 0.5 and 1.5 M.

When the diluent A and phenol B are not miscible in each other in some proportion, the upper limit for the content of phenol B is the lower of the following two limits: that mentioned above (i.e., the upper limit for phenol B, either based on mass or by mole) and the solubility limit of the phenol B in the diluent A.

The content of oligopeptide, which in the present meaning includes the case of the non-condensed amino acid, is advantageously at least $10^{-2}$ M and preferably at least 0.1 M. Higher concentrations up to the solubility limit of the oligopeptide can also be used, it being understood that it is possible to even use a suspension of oligopeptide (i.e., a concentration beyond the solubility limit) if the oligopeptide's solubility in the medium is judged insufficient by those skilled in the art.

In the preferred embodiments of the invention, at least about 0.02 moles of total peptide reactants are present, more preferably at least 0.1 moles of total peptide reactants and most preferably at least 0.5 or even better, at least 1 mole of total peptide reactant is used in the medium.

In the preferred embodiment of the invention, at least about 0.015 moles of total phenol B are present, or at least 0.02 moles of total phenol B, or at least 0.05 or at least 0.1 or even better, at least 1 mole of total phenol B is used in the medium.

The present invention also relates to a method for the synthesis of peptides, which may be protected, in a liquid medium, where the starting material is an initial peptide or amino acid, which may be protected on its acid function, and an amino acid activated on the acid function and protected on the amine function is added, in which method the reagents are dissolved in the medium according to the invention.

Similarly, the present invention also relates to a method for the synthesis of peptides, which may be protected, in a liquid medium, where the starting material is an initial amino acid or peptide, dissolved according to the invention, and a condensation reaction is carried out with another peptide having its C-terminal acid function activated and its N-terminal amine function protected, in which method the reagents are dissolved in a medium according to the invention.

For example, the amino function is protected by a carbamate group or by reaction with a β-dicarbonyl compound.

Advantageously, the acid function of the N-protected reagents is activated by an organic or inorganic acid chloride, by an alkyl chloroformate, by a carbodiimide or by an ester activated by their carbonyldiimidazole, or by an acylimidazole.

After the condensation reaction of an N-protected amino acid or peptide with the initial peptide or amino acid, the N-terminal amine function is liberated by any method and advantageously by hydrogenolysis or by acid or basic solvolysis or by photolysis.

The initial amino acid or peptide having C-terminal protection (preferably by esterification or by amidation) is generally introduced into the reaction medium, the amino acid or peptide activated on its acid function and protected on its amine function is then added, the order in which the reagents are added being arbitrary, and, after reaction, the co-products and the excess reagents are removed from the organic phase by washing with acid, basic or neutral aqueous solutions, the amine function is then liberated and, finally, a new amino acid or new peptide activated on its acid function and protected on its amine function is introduced.

Surprisingly, the medium can boost the reactivity of the peptides with the amino acids and can significantly improve the condensation kinetics.

A significant advantage of the method is that it can enable the excess reagents and the co-products from the condensation to be removed from the concentrated organic phase by simple washing with water, facilitated by the anti-emulsifying effect of phenol B, which effect was established during the study which has led to the present invention. The excess reagents are, for example, activated and N-protected amino acids or peptides, or C-protected amino acids or peptides, or catalysts serving to accelerate the coupling, such as hydroxybenzotriazole, imidazole, N-hydroxysuccinimide, etc.

The medium according to the present invention also can enable the productivity of these steps for cleavage of the protective groups to be increased. It also can enable both the cleavage of acid-sensitive groups, such as, for example, t-butoxycarbonyl, by means of commonly used reagents such as trifluoroacetic acid or hydrochloric acid, and the cleavage of hydrogenolysable groups, such as, for example, benzyloxycarbonyl, and benzyl ethers and benzyl esters or the nitro group protecting the guanidino function of the side chain of arginine, to be carried out.

The medium can permit the cleavage of base labile groups, such as sulfofluorenylmethoxycarbonyl, by commonly used reagents such as diethylamine or piperidine. It also permits the cleavage of photolysable protective groups. It also permits the cleavage of protective groups by electrochemical reduction.

A significant advantage of the method is, in homogeneous phase, that it can permit the removal of catalysts from cleavage steps by simple operations: the acid or basic catalysts may be removed by aqueous washing, while the hydrogenolysis catalysts, such as palladium absorbed on charcoal, can be removed by filtration; the peptide or peptide intermediate remaining in concentrated organic solution.

Another advantage of the dissolving method is that it is compatible with all of the operations necessary for the synthesis of peptides and that it permits a direct linking between the various steps for condensation, cleavage of protective groups and purification by washing with water without changing solvent and, if appropriate, without isolation of the peptide. It therefore permits repetitive synthesis of peptides.

Because of the repetitiveness of the synthesis, the method of the present invention can advantageously be carried out in an automated form.

The method is particularly valuable for the synthesis of peptides which are sparingly soluble in organic solvents, such as the peptides containing glycyl, arginyl, glutaminyl, asparaginyl, serinyl, threonyl and prolinyl residues.

With regard to the parameters which are not referred to in the present description, the method according to the present invention is carried out under customary conditions.

The peptides resulting from the synthesis may, if appropriate, be used for the synthesis of medicaments, vaccines, agro-foodstuff products or plant protection products.

For instance, calcitonin (No. 1611, Merck Index, 10th Ed., 1983, p. 226, hereby incorporated by reference), somatostatin (No. 8561, Merck Index, 10th Ed., 1983, p. 1246, hereby incorporated by reference), LH-RH (Luteinizing hormone-releasing factor) (No. 5306, Merck Index, 13th Ed., 1983, p. 786, hereby incorporated by reference) and thymopentin (European Patent Application Nos. 335726, 277561 A1, 282892 A2, 235904 A2, 166612 A2, and 324659 A2, hereby incorporated by reference) can all be manufactured in part by the process of the present invention.

The present invention is illustrated by the following non-limiting examples.

Protocol for dissolving experiments

The solubilities of the peptide intermediate were determined as follows, at a temperature of 25° C.

An accurately weighed amount of the peptide intermediate is placed in a Pyrex tube. The solvent or mixture of solvents to be tested is then introduced using a precision pipette so as to obtain a ratio of mass of peptide/volume of solvent of 8 g/100 cm$^3$.

The tube, closed by a screw stopper, is then placed on a HEIDOLPH agitator, TOP-MIX model, vibrating at its maximum speed for 60 seconds.

If the solid has completely dissolved, the solubility is recorded as >8 g/100 cm$^3$. If not, the volume of solvent is doubled and the procedure is started again.

At the end of 4 successive dilutions without complete dissolution, the measurements are repeated on a smaller amount of solid.

When the solubility in a given solvent was found to be less than 0.05 g/100 cm$^3$, it was also verified that heating to 40° C. and agitating for an additional 4 minutes did not change the result.

Remarks: The composition of the solvent/additive mixtures is expressed by weight.

DISSOLVING VARIOUS PEPTIDES

EXAMPLE 1

L-serinyl-L-tyrosine methyl ester hydrochloride (Ser-Tyr-OCH$_3$.HCl)

RESULTS

| | |
|---|---|
| Solubility in dichloromethane: | s < 0.05 g/100 cm$^3$ |
| Solubility in the 4/1 dichloromethane/phenol mixture: | 8 > s > 4 g/100 cm$^3$ |

EXAMPLE 2

L-tryptophanyl-L-serinyl-L-tyrosine methyl ester trifluoroacetate (Trp-Ser-Tyr-OCH$_3$.CF$_3$COOH)

The solubilities, determined as in Example 1, are as follows:

| | |
|---|---|
| in dichloromethane: | s < 0.05 g/100 cm$^3$ |
| in the 4/1 dichloromethane/phenol mixture: | 8 > s > 4 g/100 cm$^3$ |

EXAMPLE 3

L-tryptophanyl-L-serinyl-L-tyrosine methyl ester (Trp-Ser-Tyr-OCH$_3$)

Solubilities, determined as in Example 1:

| | |
|---|---|
| in dichloromethane: | s < 0.05 g/100 cm$^3$ |
| in the 4/1 dichloromethane/phenol mixture: | s > 8 g/100 cm$^3$ |
| 4/1 dichloromethane/4-t-butylphenol: | s > 8 g/100 cm$^3$ |
| 4/1 dichloromethane/2,6-dimethoxyphenol: | s > 8 g/100 cm$^3$ |
| 4/1 dichloromethane/2,6-dimethylphenol: | s > 8 g/100 cm$^3$ |
| 4/1 dichloromethane/2,6-dichlorophenol: | s > 8 g/100 cm$^3$ |
| 5/1 dichloromethane/2-hydroxypyridine: | s > 8 g/100 cm$^3$ |
| 4/1 dichloromethane/2-methoxyphenol: | s > 16 g/100 cm$^3$ |
| 4/1 dichloromethane/3-trifluoromethylphenol: | s > 8 g/100 cm$^3$ |
| 4/1 dichloromethane/2,3,4,5,6-pentafluorophenol: | s > 8 g/100 cm$^3$ |
| ethyl acetate: | s < 0.05 g/100 cm$^3$ |
| 9/1 ethyl acetate/phenol: | s = 8 g/100 cm$^3$ |

EXAMPLE 4

L-histidinyl-L-tryptophan hydrochloride (His, Trp.HCl)

Solubilities, determined as in Example 1:

| | |
|---|---|
| dichloromethane: | s < 0.05 g/100 cm$^3$ |
| 4/1 dichloromethane/phenol: | s = 2 g/100 cm$^3$ |

EXAMPLE 5

N-benzyloxycarbonyl-L-pyroglutanyl-L-histidine (Z-p Glu-His)

Solubilities, determined as in Example 1:

| | |
|---|---|
| dichloromethane: | s < 0.05 g/100 cm$^3$ |
| 4/1 dichloromethane/phenol: | 8 > s > 4 g/100 cm$^3$ |
| 4/1 dichloromethane/4-methoxyphenol: | 2 > s > 1 g/100 cm$^3$ |
| 5/1 dichloromethane/2-hdyroxypyridine: | s = 0.3 g/100 cm$^3$ |
| 4/1 dichloromethane/3-trifluoromethylphenol: | 8 > s > 4 g/100 cm$^3$ |
| 2-chlorophenol: | 8 > s > 4 g/100 cm$^3$ |
| 1/4 pentafluorophenol/dichloromethane: | 8 > s > 4 g/100 cm$^3$ |

EXAMPLE 6

L-arginyl-L-proline dihydrochloride (Afg-Pro.2HCl)

Solubilities, determined as in Example 1:

| | |
|---|---|
| dichloromethane: | s < 0.05 g/100 cm$^3$ |
| 4/1 dichloromethane/phenol: | s = 2 g/100 cm$^3$ |
| 1/1 dichloromethane/2-chlorophenol: | 2 > s > 1 g/100 cm$^3$ |

EXAMPLE 7

L-leucyl-L-arginyl-L-prolyl-glycinamide hydrochloride (Leu-Arg-Pro-Gly-NH$_2$.HCl)

Solubilities, determined as in Example 1:

| | |
|---|---|
| dichloromethane: | s < 0.05 g/100 cm$^3$ |
| 4/1 dichloromethane/4-methoxyphenol: | s = 4 g/100 cm$^3$ |
| 4/1 dichloromethane/phenol: | s = 4 g/100 cm$^3$ |
| 4/1 dichloromethane/3-trifluoromethylphenol: | s = 4 g/100 cm$^3$ |
| 2/1 dichloromethane/2-chlorophenol: | 2 > s > 1 g/100 cm$^3$ |
| 4/1 dichloromethane/2,3,4,5,5-pentafluorophenol: | 4 > s > 2 g/100 cm$^3$ |
| 2-chlorophenol: | 4 > s > 2 g/100 cm$^3$ |
| 4/1 dichloromethane/4-tert-butylphenol: | 1 > s > 0.5 g/100 cm$^3$ |
| 5/1 dichloromethane/2-hydroxypyridine: | s = 1 g/100 cm$^3$ |

By way of comparison, dimethylformamide, an additive which is not part of the invention, was tested:

| | |
|---|---|
| 4/1 dichloromethane/dimethylformamide: | s < 0.5 g/100 cm$^3$ |

EXAMPLE 8

L-prolyl-glycinamide hydrochloride (Pro-Gly-NH$_2$.HCl).

Solubilities, determined as in Example 1:

| | |
|---|---|
| dichloromethane: | s < 0.05 g/100 cm$^3$ |
| 4/1 dichloromethane/phenol: | s > 16 g/100 cm$^3$ |
| 4/1 dichloromethane/4-methoxyphenol: | 8 > s > 4 g/100 cm$^3$ |
| 2/1 dichloromethane/2-chlorophenol: | 2 > s > 1 g/100 cm$^3$ |
| 5/1 dichloromethane/2-hydroxypyridine: | 4 > 2 > 2 g/100 cm$^3$ |

By way of comparison, dimethylformamide, an additive which is not part of the invention, was tested:

| | |
|---|---|
| 4/1 dichloromethane/dimethylformamide: | s < 0.5 g/100 cm$^3$ |

EXAMPLE 9

N-E-trifluoroacetyl-L-Lysyl-L-proline (Lys-(TFA)-Pro)

Solubilities, determined as in Example 1:

| | |
|---|---|
| dichloromethane: | s < 0.05 g/100 cm$^3$ |
| ethyl acetate: | s < 0.05 g/100 cm$^3$ |
| 4/1 dichloromethane/phenol: | s > 20 g/100 cm$^3$ |
| 4/1 dichloromethane/4-tert-butylphenol: | s > 8 g/100 cm$^3$ |
| 4/1 dichloromethane/2,6-dimethoxyphenol: | s > 8 g/100 cm$^3$ |
| 4/1 dichloromethane/2,6-dimethylphenol: | s = 8 g/100 cm$^3$ |
| 5/1 dichloromethane/2-hydroxypyridine: | s > 8 g/100 cm$^3$ |
| 4/1 dichloromethane/2,6-dichlorophenol: | s > 8 g/100 cm$^3$ |
| 4/1 dichloromethane/2-methoxyphenol: | s > 8 g/100 cm$^3$ |
| 4/1 dichloromethane/3-trifluoromethylphenol: | s > 8 g/100 cm$^3$ |
| 4/1 dichloromethane/2-chlorophenol: | s > 8 g/100 cm$^3$ |
| 4/1 dichloromethane/2,3,4,5,6-pentafluorophenol: | s > 8 g/100 cm$^3$ |
| 9/1 ethyl acetate/phenol: | s = 8 g/100 cm$^3$ |

EXAMPLE 10

N-tert-butoxycarbonylpentaglycine methyl ester (Boc-Gly-Gly-Gly-Gly-Gly-OCH$_3$): (Boc-Gly$_5$-OCH$_3$)

The solubility in dichloromethane was determined by HPLC, using external standardization, on a saturated solution of Boc-Gly$_5$-OCH$_3$.

The other solubilities were determined as in Example 1:

| | |
|---|---|
| dichloromethane: | s = 0.33 g/100 cm$^3$ |
| 20/1 dichloromethane/phenol: | s = 0.5 g/100 cm$^3$ |
| 4/1 dichloromethane/phenol: | s = 4 g/100 cm$^3$ |
| anisole: | s < 0.05 g/100 cm$^3$ |
| 4/1 anisole/phenol: | s = 4 g/100 cm$^3$ |
| 2-chlorophenol: | s > 8 g/100 cm$^3$ |
| 4/1 dichloromethane/2-chlorophenol: | 2 > s > 1 g/100 cm$^3$ |
| 4/1 dichloromethane/4-methoxyphenol: | 4 > s > 2 g/100 cm$^3$ |

EXAMPLE 11

N-tert-butoxycarbonylpentaglycine benzyl ester (Boc-Gly-Gly-Gly-Gly-Gly-O-CH$_2$-Ph)

The solubility in dichloromethane was determined by HPLC, by external standardization on the supernatant of a saturated solution; the other solubilities were determined as in Example 1:

| | |
|---|---|
| dichloromethane: | s = 0.07 g/100 cm$^3$ |
| 9/1 dichloromethane/phenol: | s > 5 g/100 cm$^3$ |

By way of comparison, additives which are not part of the invention were tested:

| | |
|---|---|
| 9/1 dichloromethane/trifluoroethanol: | s < 2 g/100 cm$^3$* |
| 9/1 dichloromethane/2-octanol: | s < 2 g/100 cm$^3$* |
| 9/1 dichloromethane/pivalic acid: | s < 2 g/100 cm$^3$* |
| 9/1 dichloromethane/dimethylformamide: | s < 2 g/100 cm$^3$* |
| dichloromethane saturated with LiCl: | s < 2 g/100 cm$^3$* |

*Concentrations lower than 2 g/100 cm$^3$ were not tested.

EXAMPLE 12

Methyl N-benzyloxycarbonyl-β-benzyl-L-aspartyl-1-aminocyclopropanecarboxylate (Z-Asp-(OBzl)-Acc-OCH$_3$)

Solubilities, determined as in Example 1:

| | |
|---|---|
| methyl tert-butyl ether: | s < 0.5 g/100 cm$^3$ |
| 6/1 methyl tert-butyl ether/4-tert-butylphenol: | s > 1.2 g/100 cm$^3$ |
| chlorobenzene: | s < 1.5 g/100 cm$^3$ |
| 4/1 chlorobenzene/4-tert-butylphenol: | s > 20 g/100 cm$^3$ |
| anisole: | s > 2.5 g/100 cm$^3$ |
| 4/1 anisole/4-tert-butylphenol: | s > 25 g/100 cm$^3$ |
| ethyl acetate: | s = 2.5 g/100 cm$^3$ |
| ethyl acetate/2-hydroxypyridine (saturated solution): | 10 > s > 5 g/100 cm$^3$ |

PEPTIDE SYNTHESIS

EXAMPLE 13

Propyl L-aspartyl-1-aminocyclopropanecarboxylate (Asp-Acc-Opr)

Note: This dipeptide ester is a sweetener having a sweetening power about 200 times greater than that of sucrose according to C. Mapelli, M. Gary Newton, C. E. Ringold and C. H. Stammer, Int. J. Peptide Protein Res. 30, 489–510 (1987).

Step 1: Condensation at a concentration of 0.66 mol/liter (which is 320 g).

The following solids are charged successively into a 100 cm$^3$ three-necked Pyrex reactor cooled by a water bath at 17° C. and rendered inert by a stream of dry nitrogen, onto a stirred bed of anisole (37.5 cm$^3$):

N-benzyloxycarbonyl-B-benzyl-aspartic acid (25 mmoles),

N-ethyl-N'-(3-dimethylaminopropyl)carbodiimide hydrochloride (30 mmoles) and hydroxypyridine (42.5 mmoles).

The suspension rapidly becomes fluid and leads to a solution to which the following are added, by turns, at the end of 15 minutes:

propyl 1-aminocyclopropanecarboxylate (30 mmoles) and 4-tert-butylphenol (5 g).

After agitation overnight, the reaction mixture is washed at 30° C. with 25 cm$^3$ of 2N hydrochloric acid and then with 3 times 13 cm$^3$ of an aqueous solution consisting of 10 cm$^3$ of demineralized water and 3 cm$^3$ of brine saturated with NaCl. The combined aqueous phases are counter-extracted with 2.5 cm$^3$ of anisole.

Step 2: Hydrogenolysis of the protective groups, linked with the condensation step, The organic phase (40 cm$^3$) is transferred to a 200 cm$^3$ three-necked Pyrex reactor containing 100 cm$^3$ of distilled water and 2.8 g of 3% palladium-on-charcoal, previously rendered inert under nitrogen.

The mixture, brought to 55° C., is placed, at ambient pressure, under a stream of hydrogen for 4 hours.

Step 3: Isolation of the Peptide

The reaction mixture is filtered on Millipore 5 A and the catalyst is washed twice on the filter with 10 cm$^3$ of water at 35° C.

The organic phase is allowed to settle and removed.

The aqueous phase is washed 3 times with 30 cm$^3$ of ethyl acetate and then concentrated by distillation under vacuum to a residual mass of 60 g. Crystallization takes place spontaneously.

The suspension, to which 240 cm$^3$ of acetone are added, is filtered on a glass frit of No. 4 porosity.

The solid, washed with acetone and dried to constant weight, weighs 4.41 g.

The filtrate, concentrated to dryness, is dissolved in 11 cm$^3$ of water.

The addition of acetone (66 cm$^3$) enables a second batch of solid weighing, after drying under vacuum, 1.52 g to be isolated.

Results

Propyl L-aspartyl-1-aminocyclopropanecarboxylate monohydrate, thus obtained in a yield of 86%, is a white solid melting at 179° C.

Its $^1$H NMR spectrum recorded at 360 MHz in solution in DMSO is in agreement.

Elementary analysis: C 11, H 18, N 2, O 5, 1H$_2$O; Calculated; C 47.83; H 7.3; N 10.14; 0 34.76; Found: C 47.69; H 7.1; N 10.01; 0 34.81; Water content (Karl Fischer): 6.43%. Potentiometric determination; Amine function: 102%; Acid function: 98%.

EXAMPLE 14

By way of comparison, an experiment according to Example 13 in which either the addition of 4-tert-butylphenol or the addition of 2-hydroxypyridine is omitted rapidly leads to a reaction mixture which cannot be stirred.

PURIFICATION OF PEPTIDES BY LIQUID-LIQUID EXTRACTION

EXAMPLE 15

Glycyl-glycyl-L-phenylalanyl-L-leucine benzyl ester (Gly-Gly-Phe-Leu-OBzl)

With a view to purification of this tetrapeptide, by washing with water at the end of its synthesis, the distribution of this peptide between dichloromethane and water was studied as follows.

A solution of Gly-Gly-Phe-Leu-OBzl hydrochloride (0.9 mmole) in dichloromethane (12 cm$^3$) is stirred vigorously in the presence of an aqueous KHCO$_3$ solution (2 N; 3 cm$^3$). This mixture yields an emulsion which remains stable for several days. A comparative experiment was carried out in the presence of phenol:

EXAMPLE 16

A distribution experiment carried out in accordance with Example 15 after the addition of 3.9 g of phenol to the organic solution yields, after identical stirring, two clear liquid phases, the settling out of which is complete in less than 15 minutes.

HPLC analysis shows that the aqueous phase contains only 0.4% of the tetrapeptide employed.

EXAMPLE 17

N-tert-butoxycarbonyl-L-phenylalanyl-L-valine-benzyl ester (Boc-Phe-Val-OBzl)

The following are introduced successively at ambient temperature into a 50 cm$^3$ Pyrex glass reactor:

N-tert-butoxycarbonyl-L-phenylalanine 2-hydroxypyridine ester (3.6 moles; 1.27 g)

valine benzyl ester hydrochloride (3 mmoles; 0.73 g)

dichloromethane (15 cm³) and then, with stirring,

N-methylmorpholine (3 mmoles).

After 68 hour at ambient temperature, the reaction mixture is washed successively with 5 cm³ of dilute sulfuric acid (pH 2), with 5 cm³ of water and then with 5 cm³ of a 2N solution of $KHCO_3$ in water.

A stable emulsion then forms.

In contrast, when a dichloromethane/phenol (9/1) mixture is used as reaction solvent, all of the washings proceed without difficulty and settling out is rapid in every case.

EXAMPLE 18

Subject: Study on the influence of phenol during a peptide coupling.

Coupling studied:

Boc-Phe-O-Py+Val-OBzl.HCl+NMM
$CH_2Cl_2$ (with or without phenol)
Boc-Phe-Val OBzl+NMM.HCl

METHOD

The coupling was carried out by bringing, on the one hand, 1.2 equivalents of N-tert-butoxy-L-phenylalanine 2-hydroxypyridine ester (Boc-Phe-OPy) and, on the other hand, one equivalent of valine benzyl ester hydrochloride (Val-OBzl) into contact in methylene chloride under reflux, in the presence of N-methylmorpholine (NMM).

The disappearance of Val-OBzl and the appearance of said peptide were determined. The correlation is perfect within the limits of measurement accuracy.

The results are collated in the following table, in which the peptide yield and, which is much more significant for activation problems and kinetics, the residual Val-OBzl are shown.

Two types of experiment were carried out in a perfectly homogeneous medium, on the one hand with phenol $C_6H_5OH$ in methylene chloride (10% by mass of phenol) and on the other hand without phenol. The results show an extremely significant difference in kinetics, as 90% of said peptide is obtained in 2 hours in methylene chloride on its own and in 20 minutes in the methylene chloride/10% by mass phenol mixture.

RESULTS

The coupling yield and the percentage of Val-OBzl with time are shown in the table.

|  | TIME | 10 min | 30 min | 1 hour | 2 h. 30 m |
|---|---|---|---|---|---|
| coupling Yield | without φOH | 56% | 80% | 66% | 95% |
|  | with φOH | 78% | 93% | 96% | 99% |
| Residual Val-OBzl | without φOH | 44% | 20% | 14% | 5% |
|  | with φOH | 22% | 7% | 4% | 1% |

EXAMPLE 19

Influence of ortho-cresol on the kinetics of a peptide coupling.

REACTION

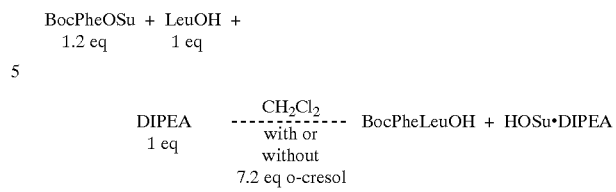

METHOD

The coupling was carried out by bringing, on the one hand, 1.2 equivalents of N-tert-butoxycarbonyl-L-phenylalanine hydroxysuccinimide ester (BocPheOSU) and 1 equivalent of free leucine (LeuOH) into contact in methylene chloride at ambient temperature, in the presence of 1 equivalent of isopropylethylamine (DIPEA).

Two types of experiment were carried out in a heterogeneous medium (leucine is insoluble), on the one hand with 7.2 equivalents of ortho-cresol and on the other hand without ortho-cresol.

The appearance of the dipeptide formed, BocPheLeuOH, was determined.

|  | Yield of BocPheLeuOH/leucine | |
|---|---|---|
| SOLVENT | 1 hour | 2 hours |
| $CH_2Cl_2$ | 9% | 17% |
| $CH_2Cl_2$/o-cresol | 57% | 72% |

The results show that ortho-cresol has a significant influence on the coupling kinetics. The formation of dipeptide in a reaction time of 1 hour is multiplied by six in the presence of ortho-cresol.

We claim:

1. A method for the synthesis of peptides in a liquid medium comprising: reacting at least one initial peptide and a second peptide in the presence of a phenol compound or a mixture of phenol compounds and at least one water-immiscible diluent A, said phenol compound or said mixture of phenol compounds being different from said water-immiscible diluent A, and said phenol compound or mixture of phenol compounds being present in an amount of at least 0.015 moles, to form a third peptide, said phenol compound or phenol compounds having a melting point of at most about 50° C.

2. The method of claim 1 where a condensation reaction is carried out between said initial peptide and said second peptide, where one of said peptides has its C-terminal acid function activated and its N-terminal amine function protected.

3. The method of claim 1 wherein the C-terminal acid function of at least one of said peptides is protected.

4. The method of claim 1 wherein the N-terminal of at least one of said peptides is protected and the acid function of said N-protected peptide is activated by at least one of the group selected from an organic or inorganic acid chloride, an alkyl chloroformate, a carbodiimide, an activated ester and an acylimidazole.

5. A method for the synthesis of a peptide in accordance with claim 1, further comprising:

cleaving any protective groups from said third peptide in the presence of said phenol compound; and purifying said third peptide by washing said third peptide with an aqueous solution in the presence of said phenol compound or compounds and said at least one diluent A.

6. A method for the synthesis of peptides in a liquid medium comprising: reacting at least one initial peptide and a second peptide in the presence of a phenol compound or a mixture of phenol compounds and at least one water-immiscible diluent A, said phenol compound or said mixture of phenol compounds being different from said water-immiscible diluent A, and said phenol compound or mixture of phenol compounds being present in an amount of at least 0.015 moles, to form a third peptide, wherein said phenol compound or phenol compounds are chosen from at least one of the group of compounds corresponding to the following formula (I):

$(R_1)n—Ar—O—H$        (I)

in which
- Ar is a monocyclic or bicyclic aromatic radical which may or may not be heterocyclic, the bicyclic ring system being either fused or not fused;
- $R_1$, which can be the same or different, is selected from:
  I. a halogen atom, or
  II. a group —Z—$R_2$, where Z can be
    a single bond; or
    an oxygen atom;
  where $R_2$ represents a hydrogen atom or an alkyl or aryl radical where either or both of said alkyl or aryl radical may be
    hyroxylated or mono- or polyhalogenated and
    have up to and including 8 carbon atoms,
  and n represents the number of substituents and is 0 or an integer at most equal to the number of positions available for substitution on the aryl radical;
  and their mixtures.

7. The method according to claim 6 wherein n>0 and at least one of $R_1$ is a halogen atom selected from the group consisting of fluorine, chlorine and bromine.

8. The method according to claim 6 wherein n>1 and at least two of the $R_1$ substituents are halogen atoms, each of which is independently selected from the group consisting of fluorine, chlorine and bromine.

9. A method for the synthesis of peptides in a liquid medium comprising: reacting at least one initial peptide and a second peptide in the presence of a hydroxyaromatic compound or a mixture of hydroxyaromatic compounds and at least one water-immiscible diluent A, said hydroxyaromatic compound or said mixture of hydroxyaromatic compounds being different from said water-immiscible diluent A, and said hydroxyaromatic compound or mixture of hydroxyaromatic compounds being present in an amount of at least 0.015 moles, to form a third peptide, wherein the amine function of at least one of either said initial peptide or second peptide is protected by at least one of the group consisting of a carbamate group and β-dicarbonyl compound.

10. A method for the synthesis of peptides in a liquid medium comprising: reacting at least one initial peptide and a second peptide in the presence of a hydroxyaromatic compound or a mixture of hydroxyaromatic compounds and at least one water-immiscible diluent A, said hydroxyaromatic compound or said mixture of hydroxyaromatic compounds being different from said water-immiscible diluent A, and said hydroxyaromatic compound or mixture of hydroxyaromatic compounds being present in an amount of at least 0.015 moles, to form a third peptide, wherein a condensation reaction is carried out between said initial peptide and said second peptide, and one of said peptides has its C-terminal acid function activated and its N-terminal amine function protected, wherein after reaction,
- the co-products and the excess reagents are removed from the organic phase by washing with at least one of acid, basic and neutral aqueous solutions,
- the amine function is then liberated and
- a fourth peptide, said fourth peptide being activated on its acid function and protected on its amine function, is introduced into the liquid medium.

11. A method for the synthesis of peptides in a liquid medium comprising:
reacting at least one initial peptide and a second peptide in the presence of a hydroxyaromatic compound or a mixture of hydroxyaromatic compounds and at least one water-immiscible diluent A, said hydroxyaromatic compound or said mixture of hydroxyaromatic compounds being different from said water-immiscible diluent A, and said hydroxyaromatic compound or mixture of hydroxyaromatic compounds being present in an amount of at least 0.015 moles, to form a third peptide, wherein the hydroxyaromatic compound is selected from the group consisting of:

hydroxypyridines, which may be monosubstituted with a straight chain or branched alkyl group having at most 6 carbon atoms;

hydroxyquinolines which may be monosubstituted with a straight chain or branched alkyl group having at most 6 carbon atoms;

monohalogenophenols;

polyfluorophenols;

phenols monosubstituted with $C_3$ to $C_4$ alkyl radicals or disubstituted by $C_1$ to $C_4$ alkyl radicals, or phenols monosubstituted or disubstituted by $C_1$ to $C_4$ alkoxy radicals, $C_1$-$C_2$ perfluoroalkyl radicals and 2,2,2-trifluoroethyl;

bis-phenols; and naphthols;

wherein each hydroxyaromatic compound has a hydroxyl group substituted on the aromatic ring structure, and wherein said diluent A is substantially inert, is not a hydroxyaromatic compound and has a solubility of at most 10% in water, and wherein the ratio by weight of said hydroxyaromatic compound to said diluent A is between 1/20 and 1/1.

12. A method for the repetitive synthesis of a peptide in a liquid medium comprising: reacting at least one initial peptide and a second peptide in the presence of a hydroxyaromatic compound or a mixture of hydroxyaromatic compounds and at least one water-immiscible diluent A, said hydroxyaromatic compound or said mixture of hydroxyaromatic compounds being different from said water-immiscible diluent A, and said hydroxyaromatic compound or mixture of hydroxyaromatic compounds being present in an amount of at least 0.015 moles, to form a third peptide, adding a fourth peptide to said medium containing said third peptide and said hydroxyaromatic compound or hydroxyaromatic compounds and said at least one water-immiscible diluent A, and condensing said peptides to form a fifth peptide in the presence of said hydroxyaromatic compound or hydroxyaromatic compounds and at least one water-immiscible diluent A.

13. The method of claim 12 for the repetitive synthesis of peptides further comprising repeating the addition and condensation of peptides in the presence of said hydroxyaromatic compound or hydroxyaromatic compounds and said at least one water-immiscible diluent A, to form a chain of peptides.

14. The method of claim 12 comprising purifying said fifth peptide by washing with an aqueous solution said fifth peptide in the presence of said hydroxyaromatic compound or compounds and said at least one diluent A.

* * * * *